Oct. 9, 1951 M. A. COOK Plant Pat. 1,044
PEAR TREE
Filed April 25, 1949
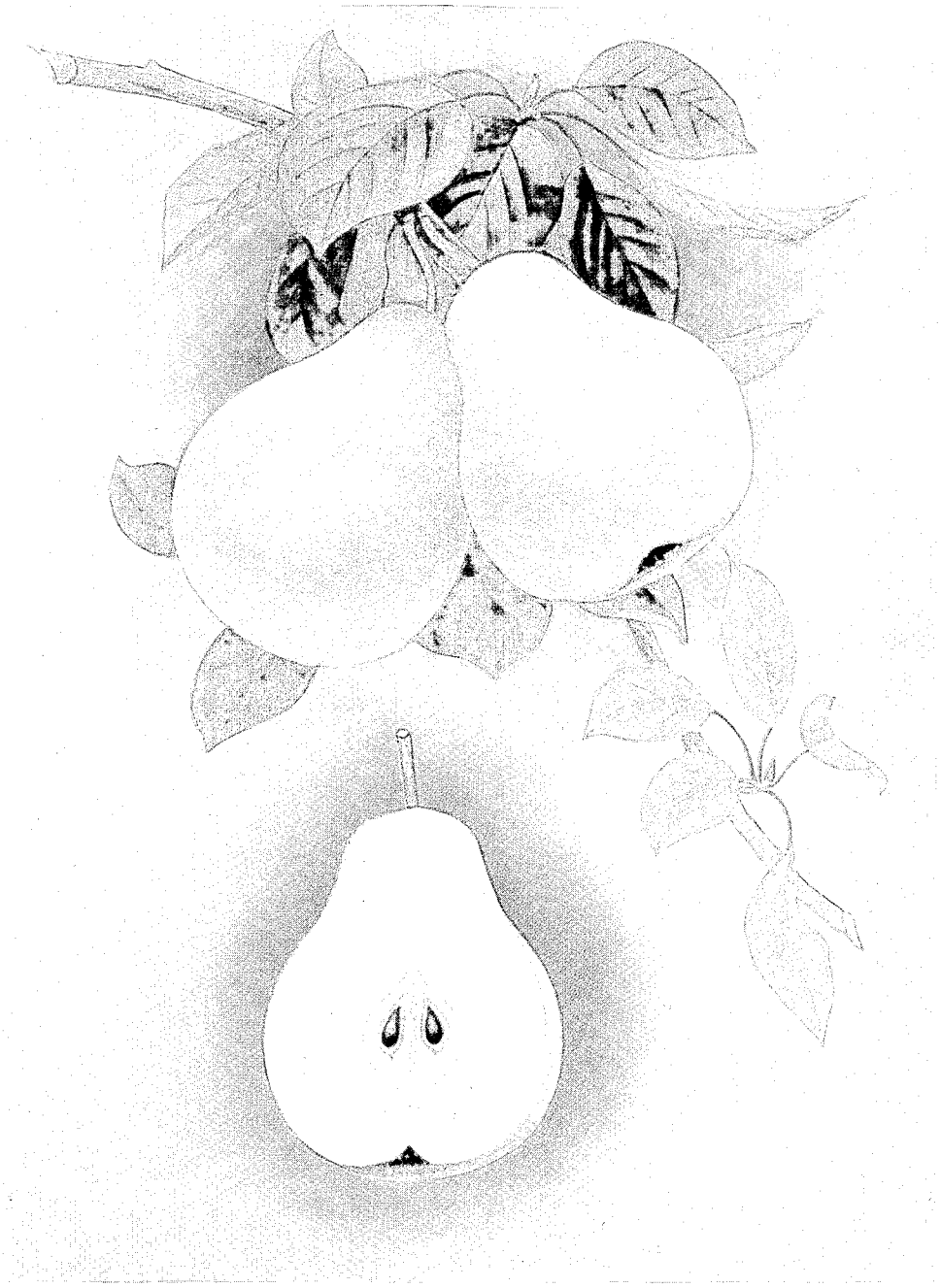
WITNESS
Addison E. Avery
INVENTOR
Marvin A. Cook
Tom Walker
ATTY.

Patented Oct. 9, 1951

Plant Pat. 1,044

UNITED STATES PATENT OFFICE 1,044

PEAR TREE

Marvin A. Cook, Tipp City, Ohio

Application April 25, 1949, Serial No. 89,493

1 Claim. (Cl. 47—62)

This invention relates to pear trees, and more particularly to a very hardy tree having a heavy green foliage and bearing unusually large, solid fruit.

Although the new tree has not been named, it was first discovered as a bud sport on my farm in Miami County, Ohio. It was immediately recognized to be a pear of exceptional merit with unusual characteristics in both the fruit and the tree.

The original sport produced unusual foliage in that the leaves were relatively large, very dark green in color with a waxy appearing surface. The bark was also unusually smooth in comparison with other known varieties.

The fruit produced was also unusual in size, color and quality. The fruit averages larger than the Bartlett pear, being between three and four and one-half inches in diameter at its base or blossom end and between five and six inches in length. The shape of the fruit is generally oblong, having a relatively long, tapering neck of reduced diameter.

Approximately ten days before complete ripening the fruit is of a uniform pea-green color, ripening to a bright yellow. When ripe, the skin of the fruit is very smooth and waxen, with few if any blemishes or other irregularities.

The flesh is quite firm, very white, sweet and juicy. The flavor is excellent. The fruit is also completely free of grit or other similar hard substances, and has a medium size core.

The fruit is excellent for eating, canning or storing. When picked during the change in color from pea-green to bright yellow and properly stored, the fruit has been kept quite successfully for a period of four months.

The present variety has been repeatedly reproduced by grafting buds from bearing trees into root stock, the resulting tree always being true to form. The tree is a very vigorous grower, the growth being both upright and generally symmetrical.

Not only is the tree a vigorous and rapid grower, but it is very hardy. Over the period of years during which the tree has been produced in the originator's orchard, it has been found that the tree is capable of withstanding winter cold and freezes, being unaffected thereby. Likewise, the tree withstands summer drought conditions quite well, being substantially unaffected thereby.

It has also been proven by experience that the new variety of pear tree disclosed herein is unaffected by any known disease to which other varieties of pear trees are susceptible in this locality.

The bark of the tree is very smooth and due to its upright and substantially symmetrical growth, very little, if any, pruning is required. The limb structure as it grows naturally is very good.

The tree buds and blooms at approximately the same time as the Kiefer pear with sufficient overlap, however, for proper pollenation. It has been found that the present new variety of pear tree is an exceptionally good pollenator for surrounding trees.

In the vicinity of Miami County, Ohio, the fruit ripens early in September, which is comparable to other high quality pears. Thus, while the fruit ripens at approximately the same time as other pears, the present fruit is of better quality and much better suited for storage and canning.

The tree is much healthier and able to withstand much worse conditions insofar as both disease and weather are concerned than other varieties bearing fruit of comparable quality.

The experimental plot of trees grown by the originator in his orchard has shown exceptionally high production and yield per tree every year since it has been in bearing. Each of the trees in the plot and the fruit produced thereon is uniform in the characteristics described herein.

The statements contained herein are based upon achievement of the noted characteristics repeatedly year after year and from an increasing number of trees. As a result of the uniformity in results and characteristics over an extended period, it is the originator's belief that the new variety of pear tree described herein is superior to any of the numerous varieties recommended for planting east of the Mississippi River.

One of the important points of superiority of the new pear tree is its freedom from blights. The experimental plot of trees has had very little attention insofar as the usual spraying is concerned, yet the trees have shown no indication of blight, particularly fire blight, to which most pear trees are quite susceptible. The fact that the new pear trees require very little spraying plus the lack of need for excessive trimming or pruning make the tree an excellent plant for orchards inasmuch as the grower need give very little time or attention to the trees after the original planting.

A more particular description of the tree and fruit is as follows:

Tree: Medium in size, varying in height from twelve to twenty feet; pyriform; upright and hardy; very productive; branches semi-stocky to stocky, smooth, greenish brown in color with few lenticels; branchlets long and short internodes, dark brown.

Leaf buds: Obtuse, free; leaves are 2½ to 3 inches long; 1½ to 2 inches wide; oval; medium thick, leathery; dark green and very waxy; apex abruptly pointed; margin finely serrate; petiole, 1½ to 2¼ inches long.

Flower buds: Large, long, plump, free; flowers are approximately 1¼ inches in diameter, showy; clusters average six buds each; pedicels ¾ inch long, very thick and green.

Fruit: Ripens very late August and early September: 3 to 4½ inches in diameter and 5 to 6 inches long; obovate-obtuse, pyriform; tapering slightly toward the apex; stem 1 to 1½ inches long, very thick, straight to curved; fleshy, the flesh being pure white, very smooth, completely free of all grit or grain, tender, sweet and very juicy; exceptional quality; cavity very shallow, narrow; calyx medium, open; calyx tube short; basin shallow, wide; skin thin, smooth, even, very glossy and waxy; color, just before ripening pea-green, ripening to a pale lemon-yellow to yellow, few dots and faint traces of dots; core, medium, closed, with clasping core lines; seeds, wide plump and acute.

Having thus described the pear tree, I claim:

A new and distinct variety of pear tree substantially as described and illustrated, characterized particularly by its large dark green waxen foliage, its vigorous growth, its resistance to known diseases and adverse weather conditions, its large bright yellow waxen fruit of substantially uniform smooth surface substantially free of blemishes and having superior keeping qualities, and the combination of the very white, firm, juicy flesh of excellent flavor and free of grit and other hard substances.

MARVIN A. COOK.

REFERENCES CITED

The following references are of record in the file of this patent:

UNITED STATES PATENTS

| Number | Name | Date |
|---|---|---|
| Pl. Pt. 380 | Silvera | Apr. 23, 1940 |
| Pl. Pt. 435 | Guraly | Dec. 17, 1940 |